(12) United States Patent
Sathian et al.

(10) Patent No.: US 10,502,882 B2
(45) Date of Patent: Dec. 10, 2019

(54) LIGHT SOURCE

(71) Applicant: Imperial Innovations Limited, London (GB)

(72) Inventors: Juna Sathian, London (GB); Mark Oxborrow, London (GB)

(73) Assignee: Imperial Innovations Limited, London (GB)

( * ) Notice: Subject to any disclaimer, the term of this patent is extended or adjusted under 35 U.S.C. 154(b) by 130 days.

(21) Appl. No.: 15/520,287

(22) PCT Filed: Oct. 21, 2015

(86) PCT No.: PCT/GB2015/053137
§ 371 (c)(1),
(2) Date: Apr. 19, 2017

(87) PCT Pub. No.: WO2016/063047
PCT Pub. Date: Apr. 28, 2016

(65) Prior Publication Data
US 2017/0329065 A1  Nov. 16, 2017

(30) Foreign Application Priority Data
Oct. 21, 2014 (GB) .................................. 1418725.6

(51) Int. Cl.
*F21V 8/00* (2006.01)
*A61B 18/00* (2006.01)
*A61N 5/06* (2006.01)

(52) U.S. Cl.
CPC .......... *G02B 6/0003* (2013.01); *G02B 6/0011* (2013.01); *A61B 2018/00589* (2013.01);
(Continued)

(58) Field of Classification Search
CPC .. G02B 6/0003; G02B 6/0011; G02B 6/0001; G02B 6/0058; G02B 6/0033;
(Continued)

(56) References Cited

U.S. PATENT DOCUMENTS 6,272,265 B1 * 8/2001 Franklin .................. F21S 11/00
   362/551
7,898,665 B2 * 3/2011 Brukilacchio ....... A61B 1/0653
   356/417
(Continued)

FOREIGN PATENT DOCUMENTS

WO    2004038465 A1    5/2004

OTHER PUBLICATIONS

International Search Report and Written Opinion issued in corresponding International Application No. PCT/GB2015/053137, dated Feb. 8, 2016.

*Primary Examiner* — Bao Q Truong
(74) *Attorney, Agent, or Firm* — Andrus Intellectual Property Law, LLP

(57) ABSTRACT

There is provided a light source arranged to output light at a first wavelength. The light source comprises a luminescent concentrator having a slab-shaped geometry. The luminescent concentrator comprises: an input port arranged to receive light and define a first area; an output port arranged to transmit light and define a second area which is smaller than the first area; and surfaces arranged to direct light inside the luminescent concentrator to the output port. The luminescent concentrator further comprises lumophores arranged to receive light at a second wavelength and emit light at the first wavelength; and a pump light supply coupled to the input port and arranged to illuminate the input port with light at the second wavelength.

18 Claims, 16 Drawing Sheets

(52) U.S. Cl.
CPC .............. *A61N 2005/0651* (2013.01); *A61N 2005/0663* (2013.01)

(58) Field of Classification Search
CPC .. A61B 2018/00589; A61N 2005/0651; A61N 2005/0663; F21V 9/30; F21V 2200/00; F21V 2200/20; F21V 2200/30
See application file for complete search history.

(56) References Cited

U.S. PATENT DOCUMENTS

| | | | |
|---|---|---|---|
| 7,982,229 B2 * | 7/2011 | Bechtel | G02B 6/0068 |
| | | | 257/98 |
| 2007/0190642 A1 | 8/2007 | Boege | |
| 2009/0078949 A1 | 3/2009 | Bechtel et al. | |
| 2009/0196046 A1 | 8/2009 | Rutherford et al. | |
| 2010/0278478 A1 * | 11/2010 | Kuo | G02B 6/2808 |
| | | | 385/24 |

* cited by examiner

LIGHT SOURCE

CROSS-REFERENCE TO RELATED APPLICATIONS

This application is the U.S. national stage application of International Application PCT/GB2015/053137, filed Oct. 21, 2015, which international application was published on Apr. 28, 2016, as International Publication WO2016/063047 in the English language. The international application is incorporated herein by reference, in entirety. The international application claims priority to GB Patent Application No. 1418725.6, filed Oct. 21, 2014, which is incorporated herein by reference, in entirety.

FIELD

The present disclosure relates to a light source or light generator. In particular, the present disclosure relates to a luminescent concentrator arranged as a light source or light generator. More particularly, the present disclosure relates to a luminescent concentrator based light source or light generator. The present disclosure also relates to an optical device for coupling radiation out of a luminescent concentrator. More particularly, the present disclosure relates to an optical coupler for a luminescent concentrator. Further particularly, the present disclosure relates to an optical device for decreasing the aspect ratio of the output aperture of a slab-shaped luminescent concentrator. The present disclosure also relates to a luminescent concentrator system and a method of processing light.

BACKGROUND

Luminance is an optical property that allows a large number of photons to pass, per unit time, through a small aperture within a small range of angles. In casual parlance, luminance is often referred to as "brightness". In engineering applications not directly concerned with the spectral sensitivity of the human eye, it is most straightforwardly measured in units of watts (of power) per square mm (of output aperture) per steradian (of solid angle): $W/(mm^2\ sr)$.

The optical power from a source of high luminance can be focussed down to a tiny spot or projected ("thrown") great distance as a collimated beam. The so-called optical Liouville theorem, also known as the "optical brightness theorem", also known as the "preservation of étendue", demands that luminance is a conserved quantity through a loss-less system of geometric optics comprising lenses and mirrors.

One might, naively, consider luminous intensity, that is the optical power per unit area of aperture, in units of $W/mm^2$ (watts per square millimetre), as a useful performance parameter. But luminous intensity, unlike luminance, is not preserved through an optical system of lenses and mirrors.

Bright sources of light enable many lucrative applications. In addition to luminance, the qualities of a light source that go to determine whether it is adequate/advantageous for a particular application include:

its spectral profile as characterized, in the case of a single emission line, by its vacuum wavelength and linewidth, both in units of nm (nanometres) or, more generally by its output spectrum in units of W/nm (watts per nanometre);

its total output power (luminous intensity integrated across its whole output aperture) in units of W (watts); and its wall-plug efficiency (optical power out divided by electrical power) in dimensionless units.

Certain optical applications—e.g. CD/DVD recording ("burning"), welding/cutting, long-distance fibre and free-space telecommunication, optical ranging/sighting and projected energy weaponry—require light sources of high luminance, i.e. in the ball park of $10^3\ W/(mm^2\ sr)$. Other applications—e.g. general room/street lighting, indicator lights, visual display panels—can suffice with luminances a million times smaller, i.e. around $10^{-3}\ W/(mm^2\ sr)$. The two values of luminescence stated here are intended only to supply a rough, quantitative sense of scale to clarify what may be meant by "high" and "low" luminance. And other applications—e.g. video projection, skin treatment and hair removal—work with what might be described as "intermediate" levels of luminance: around $1\ W/(mm^2\ sr)$.

Many familiar sources of light—such as lamps and LEDs—though powerful, do not generate light of sufficient luminance to enable high- or even intermediate-luminance applications. Sometimes these applications can be made to work at a low duty cycle by operating lamps in pulsed mode (e.g. a xenon flash lamp) or by temporarily over-driving LEDs (beyond their maximum CW operating current). But such methods have drawbacks: xenon flash lamps deteriorate with every flash (life times of 10,000 flashes are typical); and LEDs can only be over-driven by factors of a few before failing.

Stimulated emission, harnessed in devices known as lasers, is capable of generating light of extremely high luminance, both in pulses and continuously. Often, it is the only viable way of doing so. In consequence, the word/epithet "laser" has become prefixed to the names of many different applications, e.g. "laser eye surgery" and "laser ranging", that require high-luminance light. But lasers have certain drawbacks of their own: a finite pump threshold (so difficult/impossible to "simmer" at low output power), often low overall ("wall plug") energy conversion efficiency, high manufacturing cost, mechanical fragility, sensitivity to temperature changes, limited operational lifetime, and a need for skilled operators (regular re-alignment of mirrors, replacement of consumed/degraded materials). In particular, there are still certain colours of light that cannot be generated efficiently using lasers: these include cyan (around 510 nm) and from lemon yellow through to orange (550 nm to 610 nm).

Luminescent materials comprise lumophores arranged within what is otherwise an optically transparent medium. Spontaneous luminescent decay combined with total internal reflection, harnessed in devices known as luminescence (or fluorescence) concentrators ("LCs"), can generate light at luminances of a factor of 10-1000 times greater than what their pump lamps or pump LEDs can provide directly. In other words, LCs can generate up to around $10\ W/(mm^2\ sr)$ which is greater than the luminance of sunlight. Because the fluorophores or phosphors used within LCs do not need to be suitable for lasing, there is a wider choice available. As a result, LCs can be identified that output efficiently at those wavelengths lasers output inefficiently; where the difference in efficiency can exceed a factor of 10.

FIG. 1 depicts, in the 2-D space 100 spanned by output power and luminance, areas where lasers 101, lamps 105, LEDs and luminescent concentrators 103 (pumps by lamps) occupy zones of advantageous with respect to viability, manufacturing and operating costs.

LCs are advantageous in applications requiring (i) high optical powers, where wall-plug efficiency becomes a major thermal/financial consideration, but where only (ii) intermediate levels of luminance and needed, and where (iii) the spectral purity/coherence provided by lasers is also not required. Examples of applications that lie in this niche include: optical skin treatments (e.g. hair removal, spider vein removal), photo-chemical processing, optical pump sources for lasers and masers, and video projections systems.

Luminescent concentrators have been developed to direct solar energy onto photovoltaic cells. To date, they have not however been widely adopted due to poor efficiency: too much solar energy gets dissipated inside the concentrator due to "self-absorption" where light emitted from a fluorophore/phosphor gets absorbed by another fluorophore/phosphor. Self absorption has also hampered the development of efficient light sources incorporating luminescent concentrators.

FIG. 2, for example, shows the absorption 201 and fluorescence spectra 203 of Rhodamine 6G. Self-absorption is typified by the overlap between the absorption 201 and fluorescence spectra 203.

A problem is that the black absorption and red fluorescence curves overlap. The "Stokes' shift" is the difference in optical wavelength between the absorption peak and the fluorescence peak. The problem of self-absorption has been addressed in recent decades by the discovering of "high-Stokes shift" materials that suffer less self-absorption. These include organic dye molecules, inorganic quantum dots, and inorganic oxides doped with rare earths (often similar/related to those used as laser crystals/glasses). In particular, cerium-doped YAG provides a system where the absorption and fluorescence overlap very little. The absorption peak of cerium-doped YAG lies at 460 nm (and is narrow), whereas the emission peak lies at 540 nm.

Luminescent concentrators have recently been considered as light sources in U.S. Pat. Nos. 7,898,665 and 7,208,007. These patents use cylindrical or hexagonal rods of Stokes shift material. The present disclosure relates to providing a further improved light source based on a luminescent concentrator using relatively high Stokes shift materials. The present disclosure also provides an advantageous device for coupling light out of the improved light source.

SUMMARY

Aspects of the present disclosure are defined in the appended independent claims.

In summary, there is provided a light source comprising a slab-or strip-shaped luminescent concentrator.

Firstly, the inventor has identified that this new slab/strip geometry of luminescent concentrator allows for greater optical output power to be generated from a given volume of concentrator whilst allowing for effective removal of heat from all parts of the concentrator. In contrast, a rod-shaped luminescent concentrator operating at the same output aperture area, output power and luminance, would necessarily occupy a substantially greater volume.

Notably, the inventor has further recognised that upscaling the output of a slab or strip-shaped luminescent concentrator can be done by increasing the lateral width of the strip without increasing its length, nor increasing its thickness, nor without decreasing its lumophore dopant concentration. In contrast, upscaling the output power of a rod shaped luminescent concentrator involves increasing all of its dimensions, namely its diameter and length, whilst decreasing its lumophore dopant concentration, by the same common factor. Advantageously, the heat conduction path distance in a slab or strip geometry in accordance with the present disclosure does not increase with upscaling, and the area available for cooling grows proportionally with the power dissipation.

Further advantageously, the LC-based light source in accordance with the present disclosure has an output which is linear with input current. This is not the case with a laser, for example. The present disclosure therefore provides a light source having a high dynamic range output, which is easily controllable by changing current.

There is provided a light source comprising: a luminescent concentrator having a slab-shaped geometry, the luminescent concentrator comprising: an input port arranged to receive light from a pump light supply and define a first area; an output port defining a second area which is smaller than the first area; surfaces configured to direct light inside the luminescent concentrator to the output port; wherein the luminescent concentrator comprises lumophore arranged to receive light from the pump light supply at a first wavelength and emit light at a second wavelength through the output port; and a pump light supply coupled to the input port.

There is also provided a device for coupling radiation out of a luminescent concentrator. The device is arranged to receive radiation from the output aperture of a luminescent concentrator and to channel this radiation to a second aperture of a different size and/or shape. It may be considered that the optical coupler converts or changes the size/shape of the light output aperture. The device is particularly advantageous with thin sheet-shaped luminescent concentrators in which the output aperture has a high aspect ratio which may be difficult to use. The optical coupler in accordance with the present disclosure reduces the aspect ratio of the light output aperture without loss, or substantial loss, of optical energy.

Devices in accordance with the present disclosure are particularly advantageous when used with thin luminescent concentrators based on high Stokes shift materials. When operated at high power density (which is often desirable), high Stokes shift materials generate considerable heat which needs to be effectively removed. The smallness of the self-absorption afforded by high-Stokes-shifter materials such as Ce-doped YAG allows for extremely high aspect ratios of concentrator. For 0.1% doped YAG:Ce, the thickness of the concentrator in accordance with the present disclosure can be, for example, 250 microns and its length can be, for example, 1 metre.

There is also provided a luminescent concentrator arranged to receive light at a first port and redirect light to a second port, wherein the surface area of the second port is less than the surface area of the first port, the luminescent concentrator further comprising a longitudinal adiabatic taper arranged to guide light inside the luminescent concentrator to a third port, wherein the third port has an aspect ratio different to the aspect ratio of the second port.

There is also provided a luminescent concentrator comprising: a first port arranged to receive light from a light source; a second port having a surface area less than the surface area of the first port; surfaces configured to direct light inside the luminescent concentrator to the second port; a third port having an aspect ratio different to the aspect ratio of the second port; a longitudinal adiabatic taper arranged to guide light from the second port to the third port.

BRIEF DESCRIPTION OF THE DRAWINGS

Embodiments of the present disclosure will now be described with reference to the accompanying drawings in which.

In the figures, like reference numerals refer to like parts.

DETAILED DESCRIPTION OF THE DRAWINGS

It is recognised that elongate concentrators (such as U.S. Pat. Nos. 7,898,665 and 7,208,007) get too hot in the middle and suffer severe thermal stress and crack. Excessive heating of the luminescent material composing a luminescent concentrator can reduce its optical fluorescence/phosphorescence yield or cause rapid chemical degradation of the lumophore, and should therefore be avoided. Again, upscaling the output power of a rod shaped luminescent concentrator requires all its dimensions, namely its diameter and length, to be increased whilst decreasing its lumophore dopant concentration. These issues fundamentally limit the extent to which prior art elongate concentrators may be upscaled.

Embodiments of the present disclosure provide a light source comprising a substantially planar Stokes shift material. That is, one dimension of the Stokes shift material—for example, the thickness—is substantially less than at least one of the other dimensions. For example, the Stokes shift material may have a slab, sheet or strip shape. The material may be described as being substantially flat or planar.

A distinction is drawn between devices in accordance with the present disclosure and luminescent solar concentrators, LSCs, having a substantially planar configuration. LSCs are merely light conduits. That is, LSCs are not light sources or light generators. The inventors have recognised that an improved light source may be formed by coupling a high aspect ratio slab-or strip-shaped luminescent concentrator comprising lumophore to a pump light supply such as an LED array.

Figure 1:
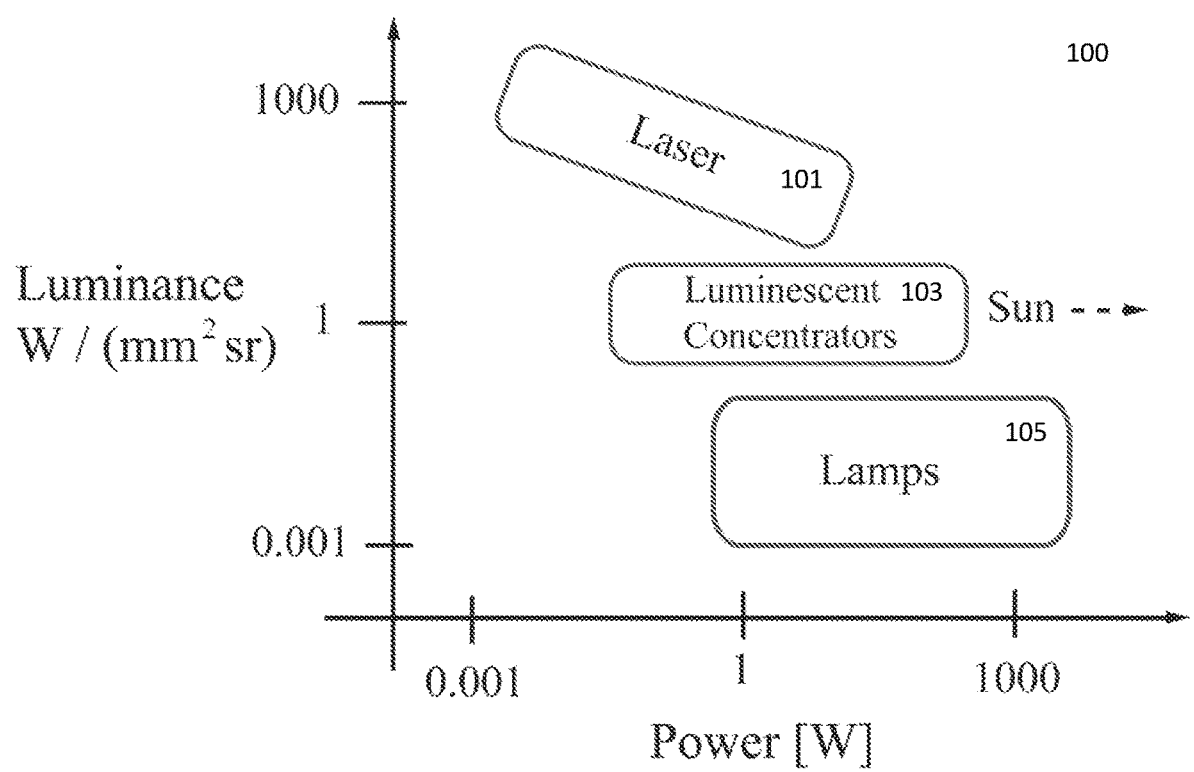
FIG. 1 shows the luminance and power output windows of lasers, luminescent concentrators and lamps.
Figure 2:
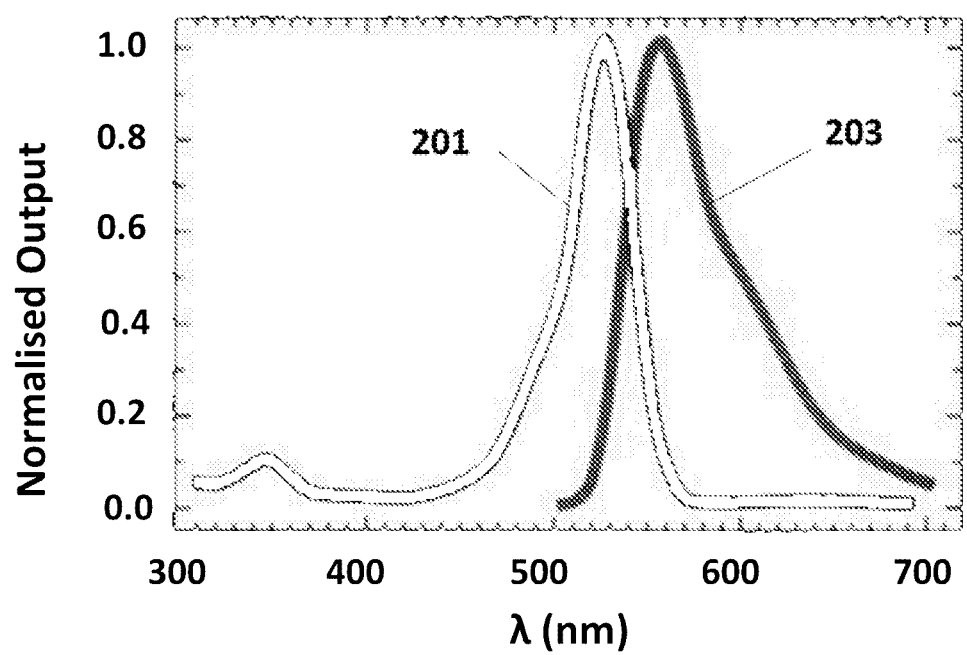
FIG. 2 shows the absorption and fluorescence spectra of Rhodamine 6G.
Figure 3A:
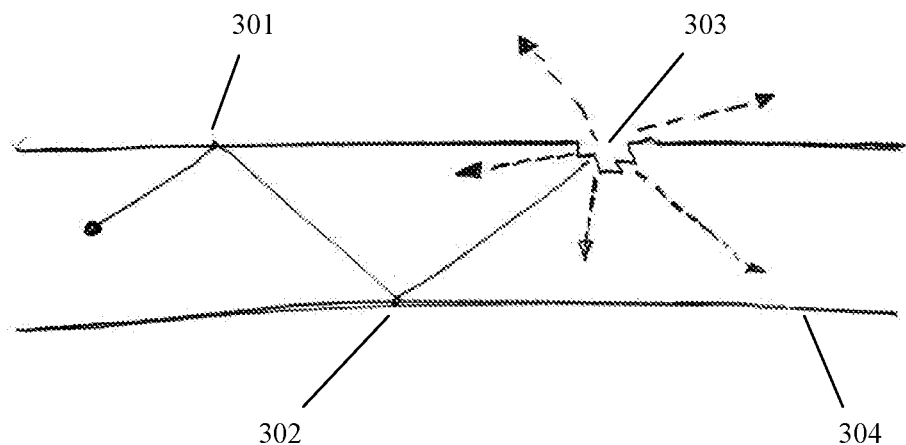
FIG. 3a illustrates the importance of surface finish on a slab-shaped luminescent concentrator.
Figure 3B:
FIG. 3b illustrates the amount of reflections occurring along the length of a slab-shaped luminescent concentrator.

However, a problem with using a thin sheet or strip concentrator as part of a light source is that the surfaces must be extremely well polished in order to avoid significant losses. As shown in FIG. 3a, light passes along the concentrator by internal reflections at points 301, 302, 303 and 304. However, as shown at point 303, any imperfection or surface roughness will cause light to be lost through, for example, scattering. As shown in FIG. 3b, this issue is particularly important in a thin sheet concentrator because of the large number of internal reflections associated with transmitting light from one end to the other. It has been recognised that certain materials, such as Ce-YAG, may be sufficiently polished to form thin luminescent concentrators based on high Stokes shift materials. Such a thin slab-shaped concentrator has a high aspect ratio output aperture.

Figure 4:
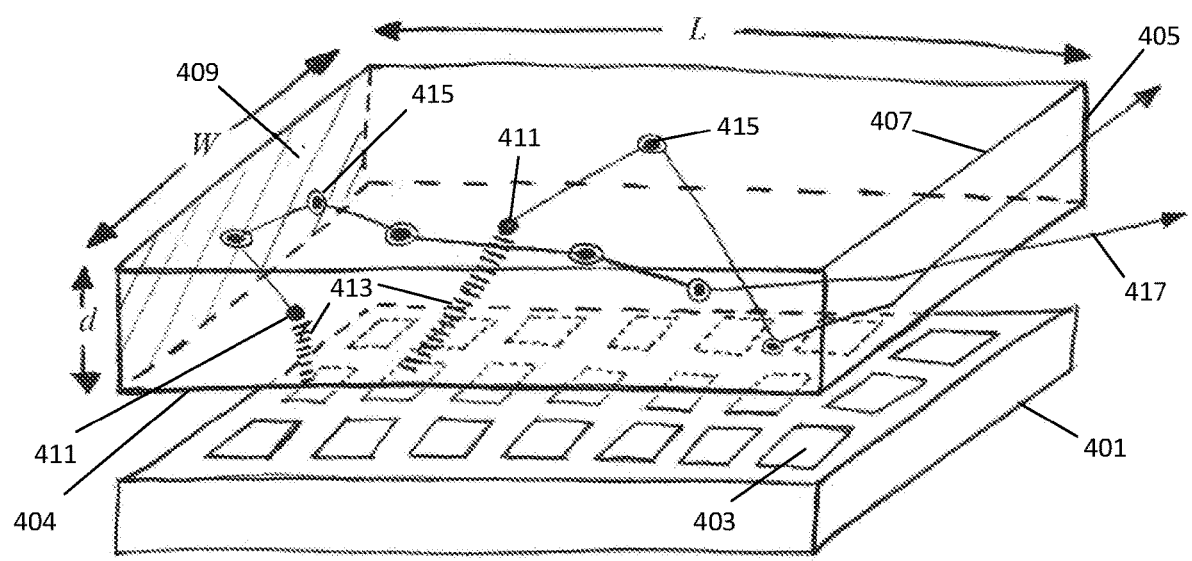
FIG. 4 shows a luminescent concentrator based light source in accordance with embodiments.

A LC-based light source in accordance with embodiments of the present disclosure is shown in FIG. 4.

FIG. 4 shows a planar LED array 401 comprising a regular array of pump LEDs 403. FIG. 4 further shows a slab-shaped luminescent concentrator 405 comprising a plurality of fluorophore ions, such as fluorophore ions 411. A largest face of the luminescent concentrator 405 forms an input port 404 arranged to engage with the output of LED array 401. The luminescent concentrator 405 has surfaces arranged to redirect light at a plurality of reflection points, such as reflection points 415, to an output port 407 formed by a smallest face of the luminescent concentrator. The other smallest face of the luminescent concentrator comprises a reflective surface 409 arranged to redirect light generated by the fluorophore ions 411 to the output port 407 of the luminescent concentrator.

In operation pump light, such as pump light 413, is generated by the pump LEDs 403 and enters the luminescent concentrator 405 through the input port 404 of the luminescent concentrator 405. By a process of fluorescence, the pump light 413 is absorbed and subsequently re-emitted at a higher wavelength by the fluorophore ions 411 in the luminescent concentrator. The re-emitted light is guided toward the output port 407 of the luminescent concentrator 405 by a series of internal reflections, such as at reflection points 415, and exits the luminescent concentrator 405 as output light 417.

FIG. 4 shows an example LC 405 in the form of a rectangular slab of length L, width W and thickness d, where this slab comprises a transparent material comprising a lumophore that absorbs light 413 received in its absorption band of wavelengths and thereupon emits light in its emissions band of wavelength, where the latter is red-shifted (longer wavelength) with respect to the former. This "lumophore" 411 may be a fluorophore (direct re-emission) or a phosphor (indirect re-emission) depending on the exact photophysics. Embodiments refer to fluorophores by way of example only The slab is optically pumped through its lower L-by-W face 404 with light from an LED array 401. Optionally, the LED array 401 may be mounted on a heat sink 401, positioned underneath the slab. A pump photon is absorbed by a lumophore 411 and thereupon emits a photon at a difference wavelength in a generally different direction to the direction of the received light. Although an LED array is shown as the pump light supply, it may be readily appreciated that any light supply may be suitable as the pump light supply.

The LC's output light 417 passes through a W-by-d face 407 (shown on the right of FIG. 4). Its opposing W-by-d face (on the left) is covered with a reflective surface 409, e.g. a mirror, which specularly reflects light back into the slab. Specular reflections on the slab's upper and lower L-by-W faces and two L-by-d side faces are achieved by total internal reflection (assuming the direction of the photon emitted by the fluorophore 411 lies outside the so-called escape cone). Light concentration is achieved because W×d<L×W.

There is therefore provided a light source arranged to output light at a first wavelength, the light source comprising: a luminescent concentrator having a slab-shaped geometry, the luminescent concentrator comprising: an input port arranged to receive light and define a first area; an output port arranged to transmit light and define a second area which is smaller than the first area; surfaces configured to direct light inside the luminescent concentrator to the output port; wherein the luminescent concentrator further comprises lumophores arranged to receive light at a second wavelength and emit light at the first wavelength; and a pump light supply coupled to the input port and arranged to illuminate the input port with light at the second wavelength.

Surfaces of the luminescent concentrator are respectively arranged such that light inside the luminescent concentrator is directed towards the output port. In embodiments, the two largest faces of the luminescent concentrator are substantially parallel.

Some relevant factors are:

(a) The aspect ratio, L/d, hence the LC's concentration factor (intensity/luminance gain) is limited by the fluorophore's self-absorption losses. It is thus advantageous to use a luminescent material such as YAG:Ce, which exhibits a high Stokes shift, hence low self-absorption.

(b) To minimize the amount of (expensive) material required for a given amount of power generated, the fluorophore-doping concentration should generally be as high as can be achieved without incurring deleterious optical scattering due to phase separation or an excessive self-absorption-to-concentration ratio significantly above its low-concentration value (due to proximity effects between nearby fluorophores).

For YAG:Ce, the above considerations lead to a preferred doping concentration of 0.01% to 0.5%. In YAG:Ce embodiments, the doping concentration is around 0.1 percent, providing an optical depth in the absorption (d) direction of a few hundred microns and an optimal length (L) in the gain direction of around 1 m.

(c) In analogy to multi-transverse laser diodes, the most effective way to increase the LC's overall output power (though not its luminance) is to extend the slab laterally: i.e. increase W and hence the number of LEDs pumping the slab.

Increasing the power by increasing the thickness (d) of the slab does not work because heat needs to be extracted conductively from the luminescent concentrator. A thin LC can be more effectively cooled. A thick LC will get too hot in the middle.

To provide tens of watts of output power using LED arrays as optical pump sources, one requires W to be several mm. In other words the geometry of the LC concentrator becomes that of a flat strip, resembling the shape (i.e. aspect ratios) of the type of pasta known as linguine where: L>>W>>d, where the output aperture W-by-d has a high aspect ratio.

In embodiments, the luminescent concentrator has a length-to-width ratio of greater than 10:1, optionally, greater than 25:1. In embodiments, the luminescent concentrator has a width to thickness ratio of greater than 7:1, optionally, greater than 10:1. In embodiments, the luminescent concentrator has a thickness of less than 1 mm, optionally, a thickness of 50 to 750 microns. In embodiments, the luminescent concentrator has a width of less than 20 mm, optionally, a width of 1 to 10 mm. In embodiments, the luminescent concentrator has a length of less than 5 m, optionally, a length of 0.05 to 2.5 m.

In embodiments, the luminescent concentrator has a rectangular parallelepiped or cuboid shape. In embodiments, adjacent sides of the luminescent concentrator are orthogonal. However, the skilled person will understand that other shapes are equally suitable. Again, by comparison, the shapes of the various LC-based light sources disclosed in U.S. Pat. Nos. 7,898,665 and 7,208,007 resemble spaghetti—that is, they are elongated rods or squares bars or hexagonal bars with cross-sections having low aspect ratios.

A distinction is also drawn between lasers and luminescent concentrators. Lasers operate by stimulated emission. Luminescent concentrators, in contrast, operate by spontaneous (non-stimulated) decay. The present disclosure relates to luminescent concentrators which also largely operate in a different luminance regime to lasers. In embodiments, the emitted light at the second wavelength has a luminance of less than 100 W/(mm$^2$ sr), optionally, 0.1 to 20 W/(mm$^2$ sr).

To date, designs of light sources based on LCs have rarely provided output powers of more than 1 W. The present disclosure provides a light source based on a luminescent concentrator capable of generating more than 10 W of optical power whilst operating continuously as well as in pulsed mode. Furthermore devices in accordance with the present disclosure can be straightforwardly scaled to higher and lower output powers.

In an embodiment, the lumophore is a fluorophore or a phosphor. In embodiments, the phosphor is $Ce^{3+}$.

In embodiments, the luminescent concentrator comprises Cerium-doped YAG "YAG:Ce", optionally, 0.05% to 0.5% Cerium-doped YAG. Advantageously, YAG:Ce suffers less from the known emission saturation effect, called drooping, when the excitation power from the pump light source is boosted up. Further advantageously, YAG:Ce is less vulnerable to heat-induced degradation compared to, for example, an organic fluorophore dissolved in transparent organic plastic such as Perspex or polystyrene. YAG:Ce also has significantly less wavelength shifting when the phosphor's working temperature changes. In embodiments, the luminescent concentrator system further comprises a planar LED array arranged to provide the light received by the input port of the luminescent concentrator. In embodiments, the LEDs output light at a wavelength of 460 nm.

In embodiments, the light source is arranged to convert blue light (450 to 495 nm) from a plurality of InGaN LEDs into a high concentration of yellow light (570 to 590 nm) using $Ce^{3+}$ ions. In this embodiment, there is provided an improved light source which is particularly advantageous for several medical applications. For example, yellow (570-590 nm) wavelengths are well absorbed by melanin and haemoglobin. Detecting the levels of haemoglobin in the blood is important in the medical field in order to diagnose and treat patients. Yellow wavelengths are particularly suitable for skin rejuvenation and acne therapy, vascular lesions, acutherapy, hemangiomas and other Light-intense/selective treatments. By way of further example, large amounts of Proto Porphyrin 9 (PPIX) exists within *P. Acnes* bacteria and PPIX is light sensitive at 578 nm, destroying the bacteria while shrinking the sebaceous gland. Yellow wavelengths may also be used to treat vascular lesions by matching the absorption of haemoglobin by rapidly photo coagulate vessels without peri vascular damage. Instant coagulation of vessels occurs and the lesions immediately disappear. The yellow wavelengths obtained in accordance with the present disclosure are also ideal to treat hemangiomas, which are vascular and thus contain high levels of haemoglobin.

The present disclosure further addresses a problem with using the slab-shaped concentrator as part of a light source. Specifically, the present disclosure addresses the problem of how to extract the light from the high aspect ratio output aperture of the slab or strip-shaped LC. For example, in applications that require delivery of the light through a light guide that can be easily deformed in all directions, one generally needs to convert the high-aspect ratio aperture at the end of the linguine-shaped LC into one of a lower aspect ratio such as a square or circle.

Figure 5:
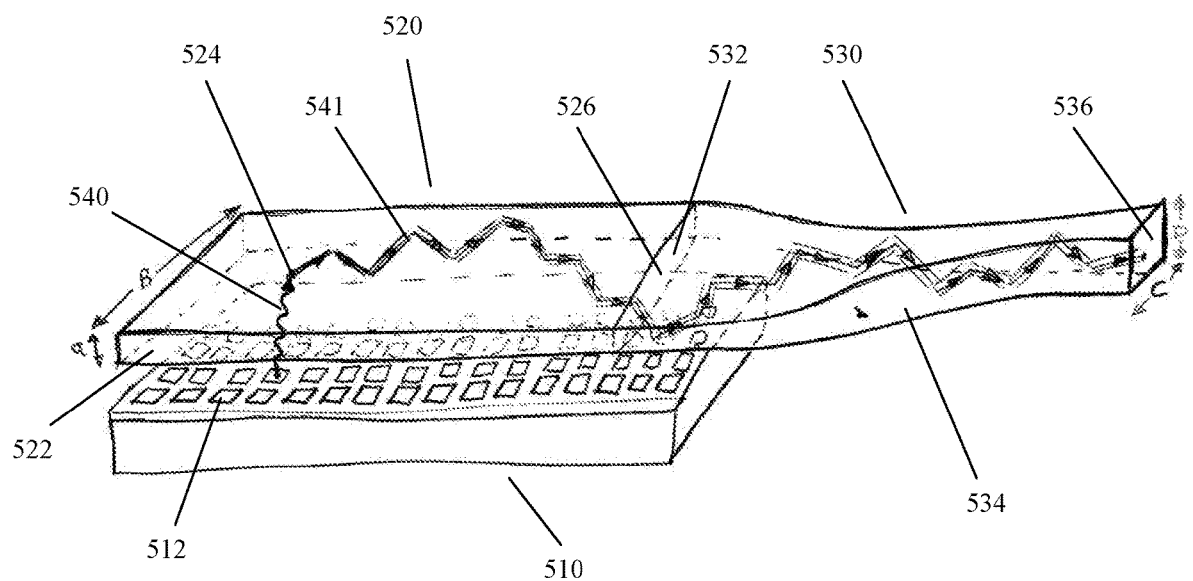
FIG. 5 shows an optical coupler and luminescent concentrator based light source in accordance with embodiments.

An embodiment of the present disclosure is shown in FIG. 5. In summary, conversion of the aspect ratio of the light output aperture is achieved by an optical coupler comprising a so-called fishtail or strip guide, as can be understood from the following.

FIG. 5 shows a planar LED array 510 comprising a regular array of pump LEDs 512. FIG. 5 further shows a slab-shaped luminescent concentrator 520 comprising fluorophore ions, such as fluorophore ion 524. A largest face of the luminescent concentrator 520 forms an input port 522 arranged to engage with the output of LED array 510. The luminescent concentrator 520 has surfaces arranged to redirect light inside the luminescent concentrator to a smallest face of the luminescent concentrator 520 to form an output port 526. FIG. 5 further shows an optical coupler 530 having a fishtail shape comprising an input port 532 and an output port 536 connected by a taper 534. The output port 526 of the luminescent concentrator 520 is coupled to the input port 532 of the optical coupler 530.

The input and output ports of the luminescent concentrator and optical coupler define respective areas each having an aspect ratio (that is, a width to height ratio). Herein, reference to the aspect ratio of a port refers to the aspect ratio of the shape or area defined by or delimited by that port. As shown in FIG. 5, the output port 526 of luminescent concentrator 520 is rectangular and has a width B and a height a, where a<<B. The input port 532 of optical coupler 530 is rectangular and also has a width B and height a. The output port 536 of optical coupler 530 is rectangular and has a width C and a height D.

The optical coupler is arranged such that:

$$a \times B = C \times D \quad (1)$$

The taper 534 expands in one direction as it shrinks in the orthogonal direction. As shown in FIG. 5, in the light propagation direction, the taper 535 increases in height as it decreases in width. The taper 534 is a gentle taper which is described as being adiabatic. There is required an adiabatic taper otherwise light loss is suffered.

The aspect ratio of the input port 532 is different to that of the output port 536. The aspect ratio of the input port 532 is relatively high because the luminescent concentrator is substantially planar. The optical coupler 530 therefore functions to gradually or gently change the aspect ratio of the light output aperture.

In operation, pump light 540 is generated by the pump LEDs 512 and enters the luminescent concentrator 520 through the input port 522 of the luminescent concentrator. By a process of fluorescence, the pump light 540 is absorbed and subsequently re-emitted at a higher wavelength by the fluorophore ions, such as fluorophore ion 524, in the luminescent concentrator 520. The re-emitted light 541 is guided toward an output port 526 of the luminescent concentrator by a process of internal reflection and thereby enters the input port 532 of the optical coupler 530. Light is then guided through the optical coupler 530 by a process of substantially lossless internal reflection toward and through an output port 536 of the optical coupler. The internal reflection process within the optical coupler 530 is substantially lossless because the taper 534 is adiabatic or, at least, substantially adiabatic.

The pattern of illumination exiting the luminescent concentrator 520 through the output port 526 has a relatively high aspect ratio owing to the slab-shaped geometry of the luminescent concentrator 520. A high aspect ratio illumination pattern is not practical in many applications. It may be understood that, in operation, the optical coupler 530 functions to change the aspect ratio of the pattern of illumination.

As shown in FIG. 5, the planar LED array 510 is arranged to substantially fill the input port 522 of the luminescent concentrator 520. It may therefore be understood that by substantially filling the input port 522, the amount of pump light 540 captured by the luminescent concentrator 520 may be at least substantially maximised.

Although FIG. 5 shows an LED array 510 operating as a pump light source and a luminescent concentrator 520 which concentrates light onto a narrow output port 526, it may be understood that the optical coupler is advantageous in its own right. Specifically, the optical coupler 530 converts or changes the aspect ratio of a light output aperture. The taper 534 of FIG. 5 is a gently, i.e. adiabatically, tapering "fishtail" that preserves cross-sectional area along its optical axis.

Figure 6A:
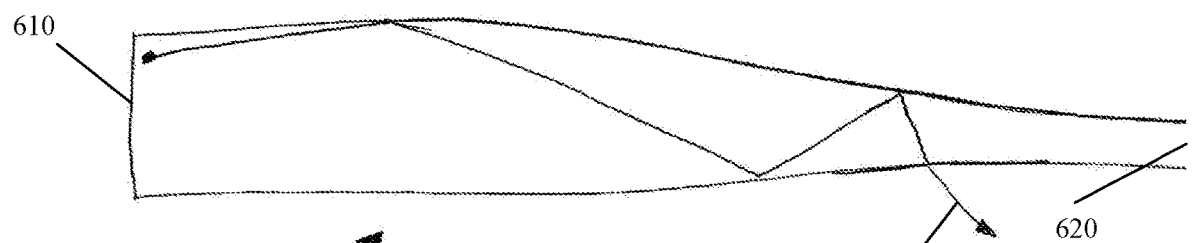
FIG. 6 shows the importance of the taper being adiabatic or quasi-adiabatic.
Figure 6B:
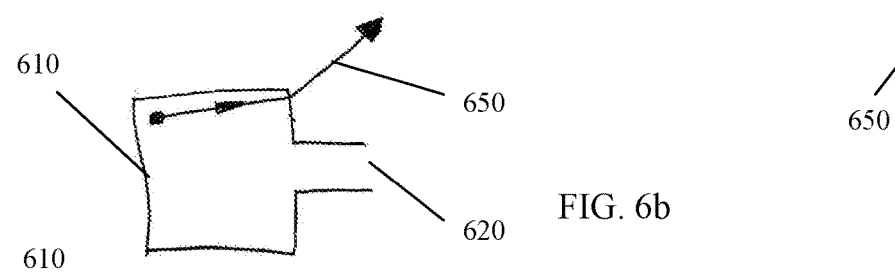
Figure 6C:
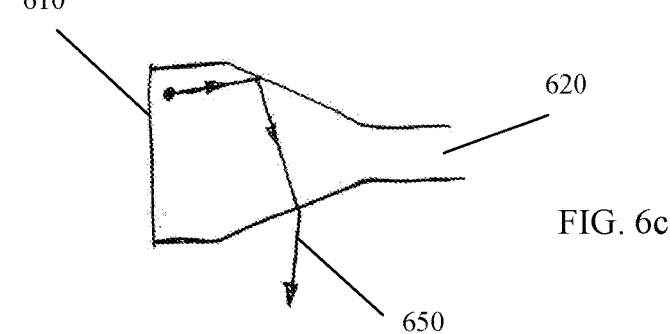

FIGS. 6a to 6c show how light may be lost from the optical coupler if the taper is not adiabatic. FIG. 6 show the optical coupler 600 having an input port 610 and output port 620. The optical coupler of FIG. 6a is of constant thickness out of the page. In FIG. 6a, light 650 is therefore lost because the optical coupler 600 does not taper in a direction out of the page. The taper of optical coupler 600 of FIG. 6b is too abrupt to guide light 650 to the output port 620 without substantial loss. The taper of optical coupler 600 of FIG. 6c is too sharp to guide light 650 to the output port 620 without substantial loss.

Figure 7:
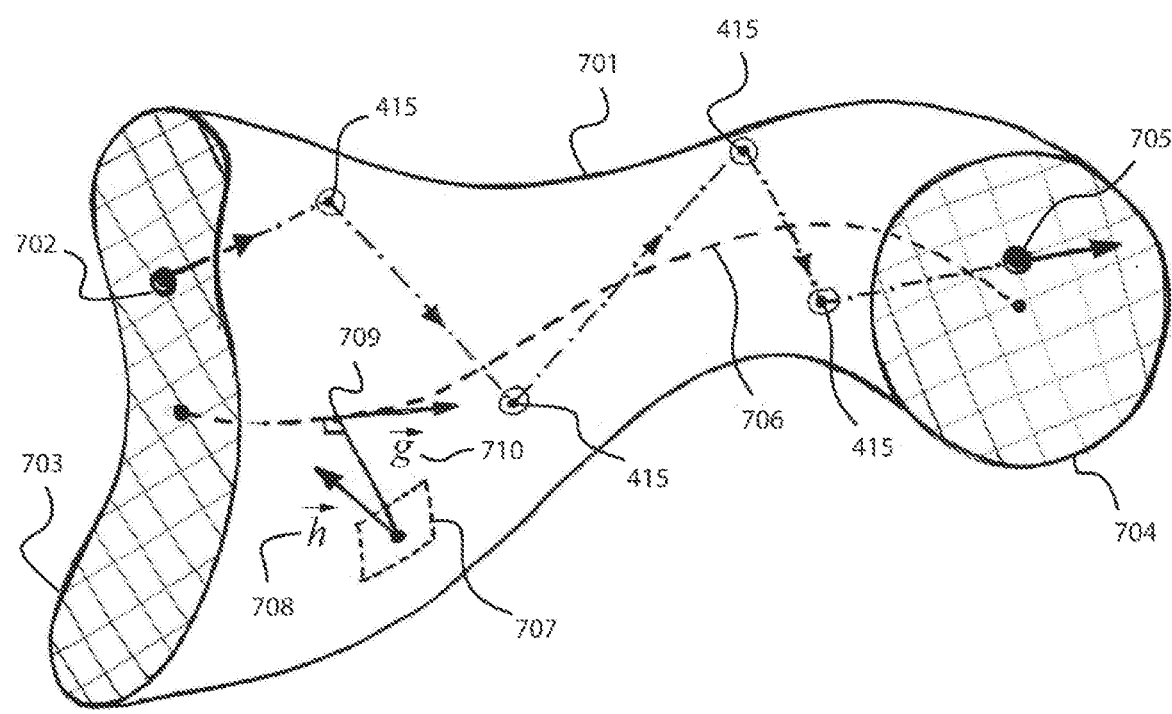
FIG. 7 shows an optical coupler with an adiabatic taper having an arbitrary cross section.
Figure 8:
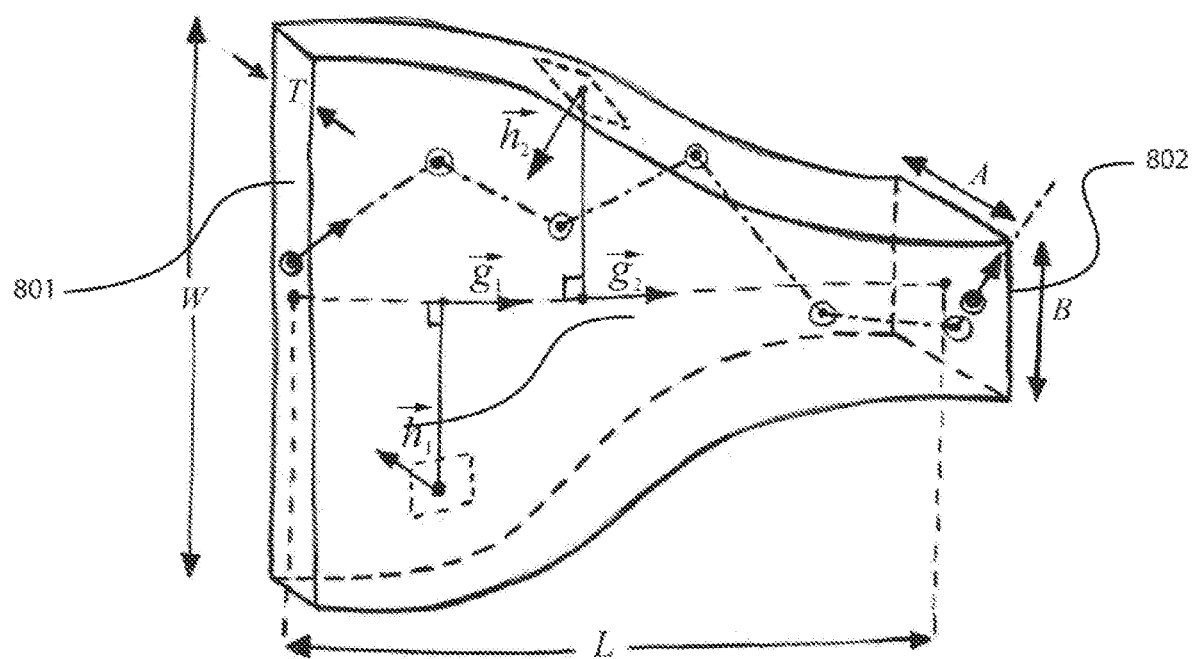
FIG. 8 shows an optical coupler with an adiabatic taper having a rectangular cross section.

FIGS. 7 and 8 show further adiabatic tapers in accordance with embodiments. An adiabatic taper may be defined as follows with reference to FIGS. 7 and 8. FIG. 7 depicts a generic adiabatic taper 701 that receives input light 702 through input aperture 703 and guides the light to leave the output aperture 704 as output light 705. The centre of the input aperture 703 and the centre of the output aperture 704 are connected by a smooth optical path 706. At any point on the surface of the taper there is in an infinitesimal patch 707, the orientation of which may be defined by its surface normal h 708. There is a closest point 709 along the optical path 706 that lies closest to the infinitesimal patch 707. At the closest point 709, there is a normalized vector g 710 that lies tangent to the optical path. The interior of the taper has a refractive index of $n_1$ and the optical medium outside of the taper has a refractive index of $n_0$. The taper is sufficiently adiabatic if:

$$h \cdot g < 0.3[1-(n_0/n_1)^2]^{1/2} \quad (2)$$

For any patch 707 on the surface of the taper, this inequality defines what is meant by a "gentle", adiabatic transition between two differently sized and/or shaped apertures. According to the optical Liouville theorem, for all of the light to reach the second aperture 704, the cross-sectional area of the output aperture 704 must be equal or greater to that of the input aperture 704. Assuming the adiabatic condition is satisfied, the power and luminance of the light crossing the input aperture 703 and output aperture 704 will be equal when their cross-sectional areas are equal.

FIG. 8 depicts a taper that quite aggressively transforms a rectangular input aperture 801 with a high aspect ratio onto a square output aperture 802 separated by a distance L. Here the tapering is sufficiently severe that the above criterion for adiabaticity may be barely satisfied. If space and material were available, a longer, gentler taper would be preferred in getting somewhat more of the light across between the two apertures. In embodiments, the taper is substantially adiabatic.

It may therefore be understood that there is therefore provided an optical coupler for a luminescent concentrator, the optical coupler comprising: a first port arranged to couple with an output port of a luminescent concentrator and define a first area; a second port defining a second area having an aspect ratio different to the first area; and a substantially adiabatic taper arranged to guide light from the first port to the second port.

Figure 9:
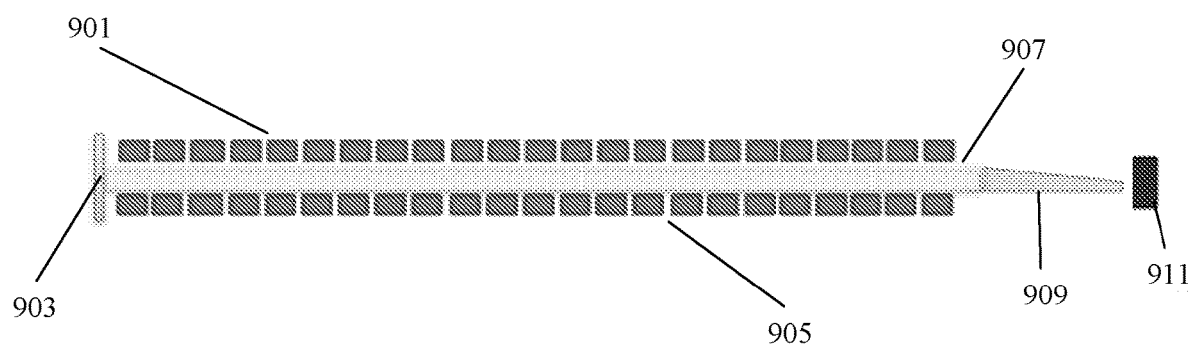
FIG. 9 shows an optical coupler and luminescent concentrator based light source in accordance with further embodiments.

A further embodiment of the present disclosure is shown in FIG. 9.

FIG. 9 shows two planar LED arrays 901, 905 each containing a regular array of pump LEDs. FIG. 9 further shows a slab-shaped luminescent concentrator 907. The largest faces of the luminescent concentrator 907 form input ports arranged to engage with the outputs of LED arrays 901, 905 respectively. The luminescent concentrator 907 has surfaces arranged to redirect light inside the luminescent concentrator to a smallest face of the luminescent concentrator 907 to form an output port. FIG. 9 further shows an optical coupler 909 having a fishtail shape comprising an input port and an output port connected by a taper. The output port of the luminescent concentrator 907 is coupled to the input port of the optical coupler 909.

FIG. 9 further shows a mirror 903 arranged to redirect light exiting the other smallest face of the luminescent concentrator 907 back into the luminescent concentrator. However, mirror 903 is optional. FIG. 9 also shows a detector 911 which is, of course, only shown for illustrative purposes.

It may therefore be understood that the luminescent concentrator may receive input light through one or more of its surfaces. Again, advantageously, the largest face or faces of the luminescent concentrator may be used as an input so as to maximise the output.

In other embodiments, at least one of the largest surfaces of the luminescent concentrator is used to cool to the luminescent concentrator. This is advantageous because the largest surface has the largest surface area.

In embodiments, the LEDs of the LED array are InGaN pump LEDs emitting light at a wavelength centred at approximately 460 nm. In embodiments, the luminescent concentrator is made of approximately 0.1% Ce-doped YAG in which $Ce^{3+}$ ions function as a phosphor. In embodiments, the optical coupler is made of Schott SF57 glass, the refractive index of which is a good match to that of YAG. In these embodiments, the device is arranged to receive blue light and output high concentration yellow light. However, the skilled person will understand that the choice of LEDs and materials is based on the required output of the device—in particular, the required wavelength of the output.

An advantage of the optical coupler in accordance with embodiments is that it provides a more useable output light pattern. Specifically, a more useful lower aspect ratio light pattern is created from a less useful higher aspect ratio light pattern.

In embodiments, the aspect ratio of output port of the optical coupler is less than the aspect ratio of the input port of the optical coupler. That is, the aspect ratio of the second area is less than the aspect ratio of the first area. Accordingly, the high aspect ratio output port of a slab-shaped luminescent concentrator may be converted into a more useful lower aspect ratio without substantial loss of optical energy. In these embodiments, the lower aspect ratio of pattern of illumination produced by the optical coupler is more useful for at least some applications.

In embodiments, the first port of the optical coupler is arranged to couple with a high aspect ratio output port of a luminescent concentrator. That is, the optical coupler is particularly advantageous when the output port of the luminescent concentrator defines an area having a relatively high aspect ratio because such as aspect ratio is generally impractical for most applications. It may be understood that the optical coupler may be arranged to couple with any device having an output port.

In embodiments, the cross-sectional area of the optical coupler is preserved along the length of the optical coupler. However, it may be understood that the device will still function if this condition is not satisfied but optical energy will be lost.

The taper of the optical coupler may be described as having a fishtail shape owing to its physical shape.

In embodiments, the optical coupler has a rectangular output port. However, the output port may have any shape including circular or elliptical.

It may be understood that light is guided along the taper of the optical coupler by internal reflection. In advantageous embodiments, the taper is arranged such that the internal reflections are total internal reflection so as to minimise energy loss.

Advantageously, the optical coupler is passive. For example, the optical coupler does not require an electrical power supply.

In embodiments, there is provided an improved luminescent concentrator system comprising the light source and the optical coupler. The light source comprises an input port arranged to receive light from a light supply and an output port. The input port defines a third area and the output port defines a fourth area. The fourth area is smaller than the third area so concentration of light is achieved. The surfaces of the luminescent concentrator are configured to direct light inside the luminescent concentrator to its output port.

In embodiments, the optical coupler of the present disclosure is coupled with a slab, sheet or strip shaped luminescent concentrator. These embodiments provide a luminescent concentrator system which solves problems related to the size and shape of the output optical aperture of a high aspect ratio luminescent concentrator.

Figure 10:
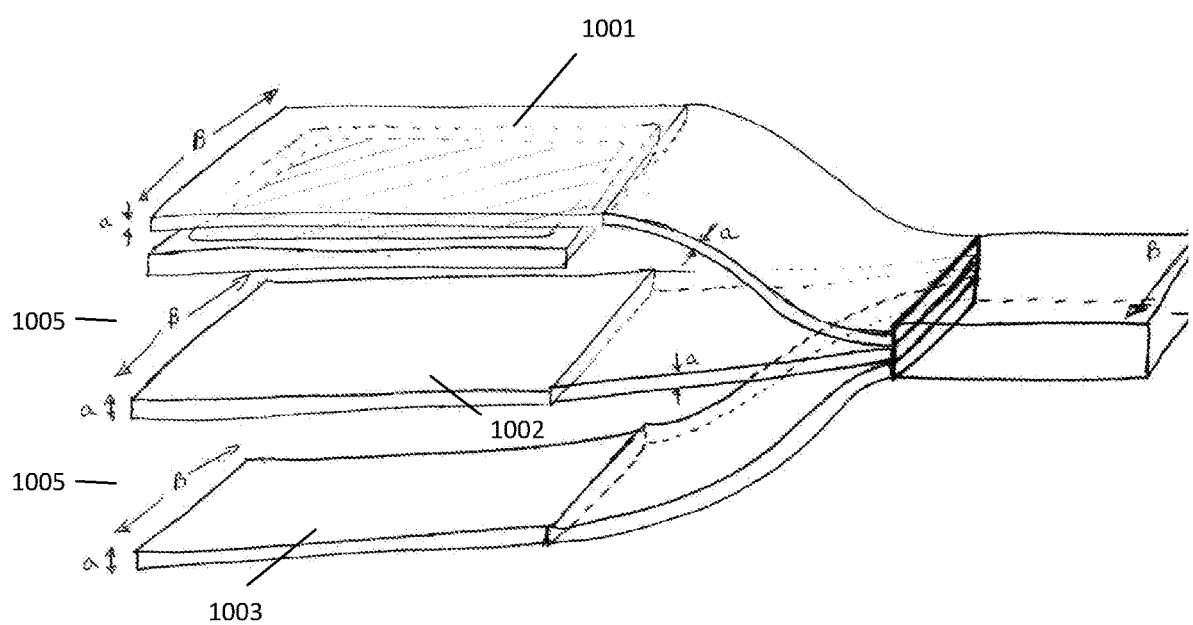
FIG. 10 shows a 3-ganged concentrator in accordance with embodiments.

In a further advantageous embodiment, the luminescent concentrator system comprises a plurality of luminescent concentrators having a common output port. FIG. 10 shows an example of first 1001, second 1002 and third 1003 luminescent concentrators being coupled together in this fashion. Such an arrangement of stacked multiple luminescent concentrators allows for a more spatially compact light generator than one incorporating just a single planar concentrator supplying the same output aperture area and power. Note, however, that gaps 1005 need to be maintained between the individual luminescent concentrators within such a stack: to allow for a flow of forced air or liquid coolant.

Figure 11:
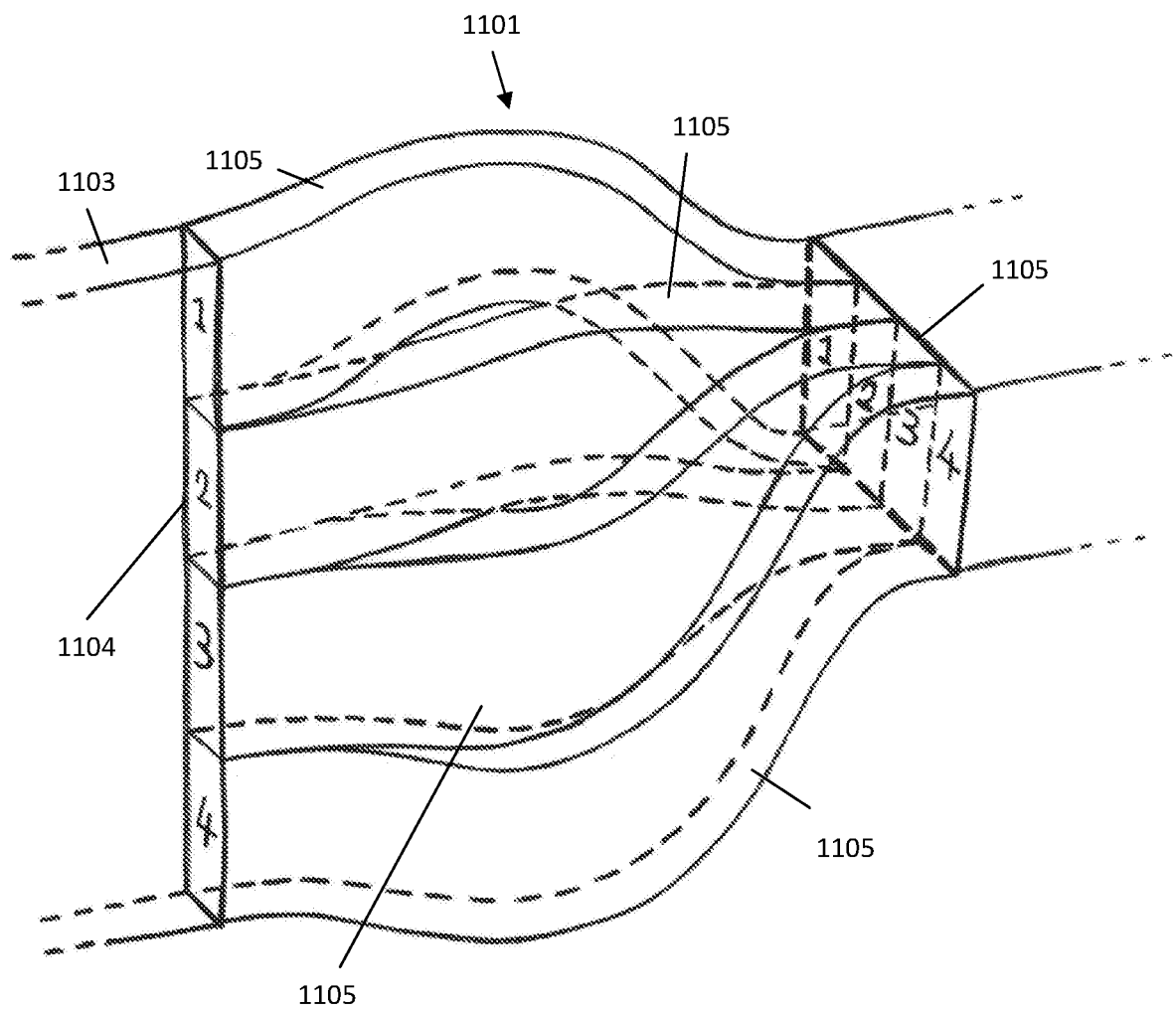
FIG. 11 shows a strip guide converter in accordance with embodiments.

The requirement of an adiabatic taper, such as the one shown in FIG. 5, for converting light flowing across an aperture of high aspect ratio to light flowing across an aperture of a lower aspect ratio, imposes a large spatial footprint due to the required length L of the taper. But this length can be reduced, as shown in FIG. 11, by using a so-called "strip guide" 1101 that splits the high-aspect-ratio output aperture 1104 of the fluorescent concentrator 1103 into several quasi-prismatic strip guides 1105 which thereupon feed a lower aspect ratio aperture 1107. Note that the individual strips 1105, being quasi-prismatic, easily satisfy the criterion for adiabaticity. This space-saving coupler comes at the price of additional manufacturing complexity.

It may be understood that there is a provided a method of processing light. In embodiments, the method is a method of producing high brightness radiation from a plurality of lower brightness sources. In other embodiments, the method is a method of converting light from a plurality of blue LEDs into high concentration yellow light. The first step of the method comprises receiving light at a first wavelength through a first port defining a first area. The second step comprises converting light to a second wavelength. The third step comprises directing light to a second port defining a second area which is smaller than the first area. The first, second and third steps are performed by a luminescent concentrator. The fourth step comprises receiving light from the second port. The fifth step comprises directing light using a longitudinal adiabatic taper to a third port having an aspect ratio different to the aspect ratio of the second port. The fourth and fifth steps are performed by an optical coupler.

In an embodiment, the first wavelength is in the range 450 to 495 nm and the second wavelength is in the range 570 to 590 nm. Yellow wavelengths are advantageous for at least the reasons set out above. In embodiments, the method further comprises the step of illuminating biological tissue with light emitted from the third port. In an embodiment, the step converting light to a second wavelength is performed by a fluorophore.

Although embodiments describe a light source and luminescent concentrator in which the wavelength of light is changed by fluorescence, for example, it may be understood that advantages provided by the optical coupler are provided regardless of wavelength or wavelength conversion within the luminescent concentrator. That is, although embodiments refer to specific wavelengths of radiation, it may be understood that the light source, optical coupler, luminescent concentrator and luminescent concentrator system of the present disclosure are equally suitable for any wavelength of electromagnetic radiation.

Although aspects and embodiments have been described above, variations can be made without departing from the inventive concepts disclosed herein.

EXAMPLES

Experimental results include an improved light source based on a Cerium doped Yttrium Aluminium Garnet (Ce:YAG) luminescent concentrator (LC) with a slab or strip shaped geometry.

Figure 12:
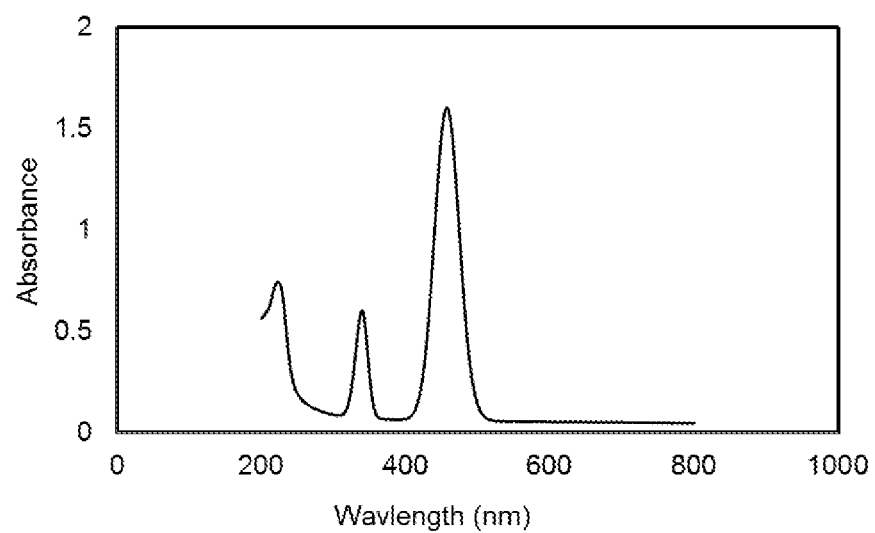
FIG. 12 shows a UV-Vis absorbance measurement of a Ce:YAG crystal to determine the cerium concentration in accordance with the disclosed examples.

The Ce:YAG crystal boule was obtained from Union Carbide, Wash., USA. The concentration of cerium was determined to be approximately 0.1% using Agilent Cary 5000 UV-Vis-NIR spectrophotometer (FIG. 12). The Ce:YAG crystal was cut into slabs or strips and polished at SurfaceNet GmbH, Germany. The geometry of the concentrator is slab or strip shape, which allows better light collection efficiency and effective heat removal from the concentrator at high input powers. The final polishing of the Ce:YAG slabs were done at IC Optical Systems Ltd, UK.

Figure 13:
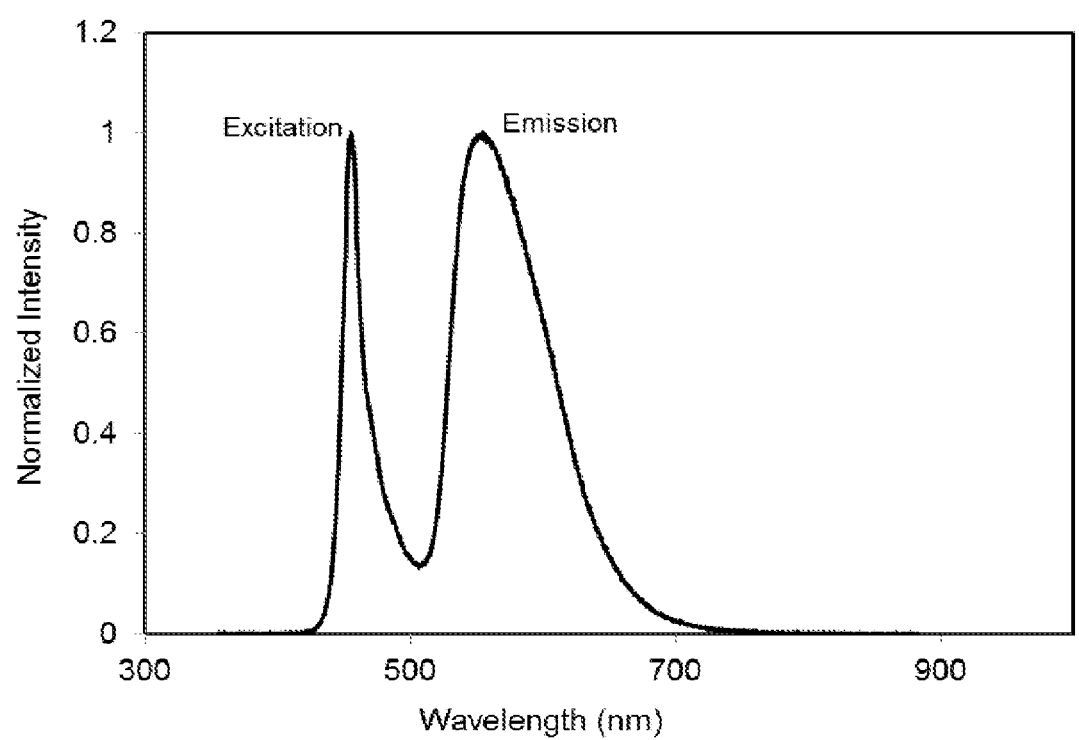
FIG. 13 shows the emission spectrum of a Ce:YAG luminescent concentrator on excitation with blue InGaN LEDs in accordance with the disclosed examples.

Experiments have been conducted in two steps, first using a single slab or strip LC with dimensions~(76×4.3×0.57) mm. This means a length-to-width ratio of 17.7:1 and width-to-thickness ratio of 7.5:1. The single LC slab was excited simultaneously from the top and bottom surfaces; the (76×4.3) mm surfaces, using commercially available 50 W InGaN LEDs outputting blue light at a wavelength of ~460 nm. The LEDs were mounted on a water-cooled Aluminium-Copper heat sink (PSL Assemblies Ltd, UK) using thermally-conductive epoxy. In effect, the slab concentrator is sandwiched between the two LED arrays (FIG. 9) with adequate space in between the LED arrays for forced air cooling of the Ce:YAG slab at high input powers. The final output from the LC was collected from the (4.3×0.57) mm edge using an optical coupler, here an adiabatic taper made of SF57 glass whose refractive index is close to the Ce:YAG. The SF57 adiabatic taper was made at IC Optical Systems Ltd, UK. The Ce:YAG slab and the optical coupler are attached using an index matching liquid bought from Pixelligent Technologies LLC, MD, USA, which minimizes the light losses. The CW output optical power measured with a single LC is close to 4 W, in a broad spectrum ranging from 500-700 nm where ~20% of this falls in the 570-590 nm yellow region. FIG. 13 shows the excitation and emission spectrum of the LC light source measured using an Ocean Optics USB2000+ spectrometer.

Figure 14:
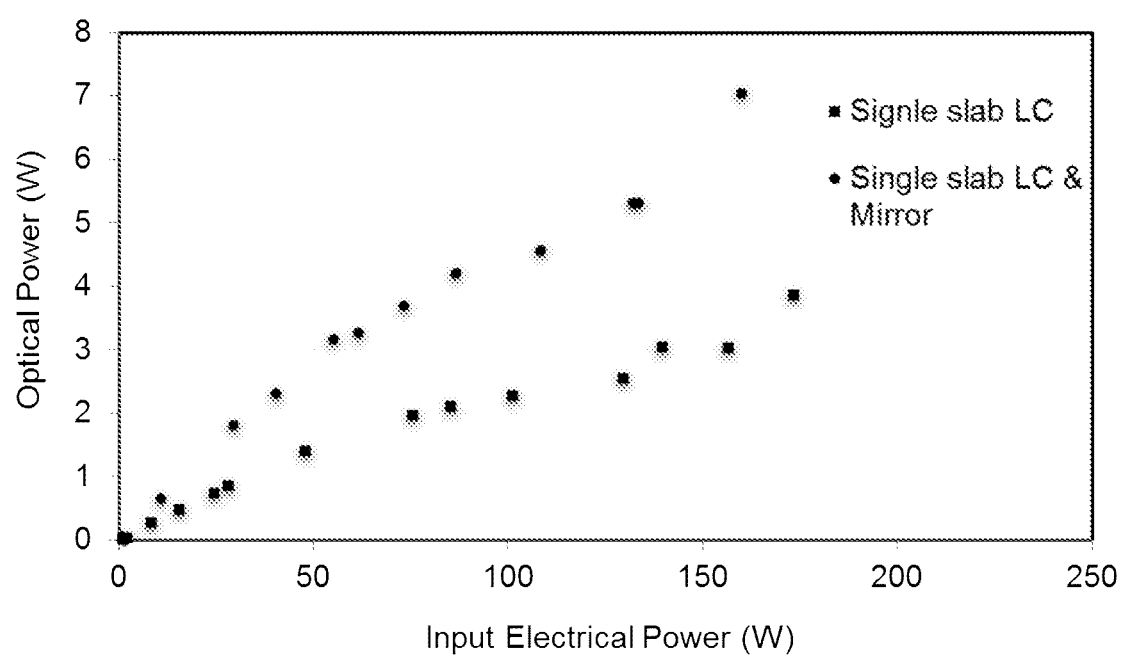
FIG. 14 shows the optical output power for a single slab Ce:YAG luminescent concentrator in accordance with the disclosed examples.

The optical power measurements were done using an integrating sphere with a silicon detector attached to its output port. The wall plug efficiency (WPE) of the single LC set-up combined with a mirror at the opposite edge of the Ce:YAG slab-optical coupler light source is on average~5.0%, which is much higher than a laser. The experimental results are shown in FIG. 14.

Figure 15:
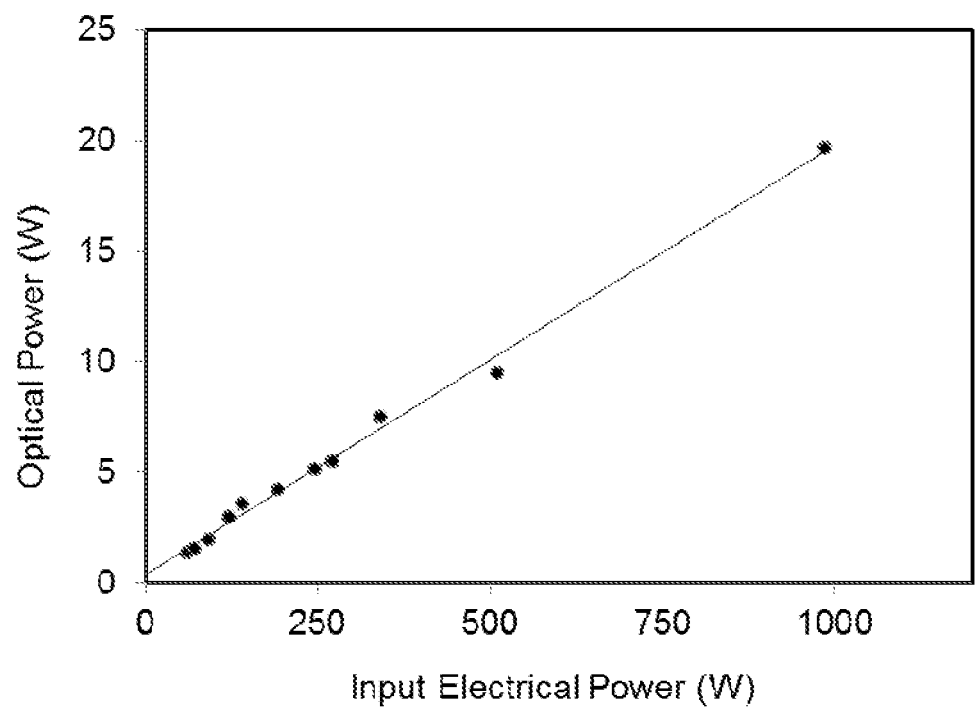
FIG. 15 shows the optical output power for a four slab Ce:YAG luminescent concentrator in accordance with the disclosed examples.

A more advantageous option to upscale the output power is to increase the lateral width of the concentrator, but here, instead, the length of the concentrator has been increased by attaching additional Ce:YAG slabs of same dimensions, using the same index matching liquid, to the single Ce:YAG-optical coupler light source set-up. Hence the present light source consists of four Ce:YAG slabs and the optical coupler. FIG. 15 shows the optical output power for a four slab Ce:YAG luminescent concentrator.

The improved light source effectively increased the CW output power to close to 20 W, still maintaining a WPE>2.0%, which corresponds to an output intensity of 6.5 W/mm$^2$ (FIG. 15). The decrease in WPE accounts to the self-absorption (still small due to the high Stokes shift) and losses at the joints. A mirror at the back end of the fourth Ce:YAG slab increased the output an additional 15% only, due to these losses.

Figure 16:
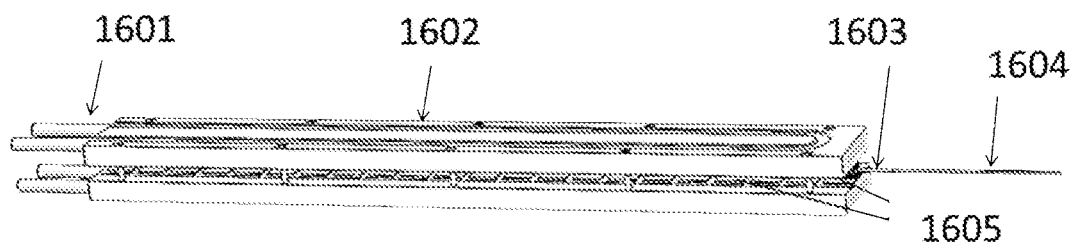
FIG. 16 shows the basic set-up of the LC light source in accordance with the disclosed examples.

FIG. 16 shows the basic set-up of the LC light source including copper tubes for water inlet 1601, LED heat sink 1602, Ce:YAG crystal 1603, SF57 optical coupler 1604 and InGaN LEDs 1605.

The invention claimed is:

1. A light source arranged to output light at a first wavelength, the light source comprising:

a luminescent concentrator having a slab-shaped geometry with a width to thickness ratio of greater than 7:1, the luminescent concentrator comprising:
an input port arranged to receive light and define a first area;
an output port arranged to transmit light and define a second area which is smaller than the first area;
surfaces arranged to direct light inside the luminescent concentrator to the output port;
wherein the luminescent concentrator further comprises lumophores arranged to receive light at a second wavelength and emit light at the first wavelength; and
a pump light supply coupled to the input port and arranged to illuminate the input port with light at the second wavelength.

2. The light source as claimed in claim 1 wherein the luminescent concentrator has a length to width ratio of greater than 10:1.

3. The light source as claimed in claim 1 wherein the luminescent concentrator has a thickness of less than 1 millimeter.

4. The light source as claimed in claim 1 wherein the luminescent concentrator has a width of less than 20 millimeters.

5. The light source as claimed in claim 1 wherein the luminescent concentrator has a length of less than 5 meters.

6. The light source as claimed in claim 1 wherein the emitted light at the second wavelength has a maximum luminance of less than 100 watts per square millimeter per steradian.

7. The light source as claimed in claim 1 wherein the lumophore is a fluorophore or a phosphor.

8. The light source as claimed in claim 1 wherein the luminescent concentrator comprises Cerium-doped YAG.

9. The light source as claimed in claim 1 wherein the light supply is a planar LED array.

10. A luminescent concentrator system comprising:
the light source of claim 1; and
an optical coupler comprising:
    a first port arranged to couple with an output port of the luminescent concentrator and define a first area;
    a second port defining a second area having an aspect ratio different to the first area; and
    a substantially adiabatic taper arranged to guide light from the first port to the second port.

11. The luminescent concentrator system as claimed in claim 10 wherein the aspect ratio of the second area is less than the aspect ratio of the first area.

12. The luminescent concentrator system as claimed in claim 10 having a fishtail shape.

13. The luminescent concentrator system as claimed in claim 10 arranged such that light is guided along the substantially adiabatic taper by internal reflection.

14. The luminescent concentrator system as claimed in claim 10 wherein the optical coupler is passive.

15. A luminescent concentrator system comprising:
a light source of claim 1 and further comprising:
an optical coupler having:
    a first port arranged to couple with the output port of the luminescent concentrator, wherein the first port defines a first area with a first aspect ratio;
    a second port that defines a second area having a second aspect ratio that is different than the first aspect ratio; and
    an adiabatic taper arranged to guide the light from the first port to the second port.

16. A method of processing light, the method comprising the following steps:
receiving the light at a first wavelength with a luminescent concentrator having a slab-shaped geometry with a width to thickness ratio of greater than 7:1 and a first port that defines a first area through which the light is received;
converting the light to a second wavelength; and
directing the light at the second wavelength to a second port of the luminescent concentrator that defines a second area which is smaller than the first area;
receiving the light at the second wavelength from the second port with an optical coupler having a longitudinal adiabatic taper and a third port; and
directing the light at the second wavelength using the longitudinal adiabatic taper to the third port that has an aspect ratio that is different than the aspect ratio of the second port.

17. The method as claimed in claim 16 wherein the first wavelength is in the range 450 to 495 nanometers and the second wavelength is in the range 570 to 590 nanometers.

18. The method as claimed in claim 16 wherein the step of converting the light to a second wavelength is performed by a fluorophore.

\* \* \* \* \*